United States Patent
Jones et al.

[11] Patent Number: 5,823,198
[45] Date of Patent: Oct. 20, 1998

[54] METHOD AND APPARATUS FOR INTRAVASCULER EMBOLIZATION

[75] Inventors: Michael L. Jones, Capistrano Beach, Calif.; Richard J. Greff, St. Petersburg, Fla.

[73] Assignee: Micro Therapeutics, Inc., San Clemente, Calif.

[21] Appl. No.: 690,075

[22] Filed: Jul. 31, 1996

[51] Int. Cl.⁶ .................................................... A61B 19/00
[52] U.S. Cl. ............................................................... 128/899
[58] Field of Search ................................. 128/899; 623/1

[56] References Cited

U.S. PATENT DOCUMENTS

| | | |
|---|---|---|
| 4,708,718 | 11/1987 | Daniels . |
| 4,979,947 | 12/1990 | Berman . |
| 4,994,069 | 2/1991 | Ritchart et al. . |
| 5,007,926 | 4/1991 | Derbyshire . |
| 5,078,726 | 1/1992 | Kreamer . |
| 5,092,877 | 3/1992 | Pinchuk . |
| 5,100,422 | 3/1992 | Berguer et al. . |
| 5,207,695 | 5/1993 | Trout, III . |
| 5,211,658 | 5/1993 | Clouse . |
| 5,213,580 | 5/1993 | Slepian et al. . |
| 5,250,071 | 10/1993 | Palermo . |
| 5,304,194 | 4/1994 | Chee et al. . |
| 5,304,195 | 4/1994 | Twyford, Jr. et al. . |
| 5,354,295 | 10/1994 | Guglielmi et al. . |
| 5,356,432 | 10/1994 | Rutkow et al. . |
| 5,405,379 | 4/1995 | Lane . |
| 5,407,423 | 4/1995 | Yoon . |
| 5,423,851 | 6/1995 | Samuels . |
| 5,456,693 | 10/1995 | Conston et al. . |
| 5,460,621 | 10/1995 | Gertzman et al. . |
| 5,603,698 | 2/1997 | Roberts et al. . |

FOREIGN PATENT DOCUMENTS

| | | |
|---|---|---|
| 0547530 | 6/1993 | European Pat. Off. . |
| 3644588C1 | 3/1988 | Germany . |
| WO 94/06460 | 3/1994 | WIPO . |

OTHER PUBLICATIONS

Polyvinyl Alcohol (Ivalon)—A New Embolic Material, by S. Murthy Tadavarthy, MD., James H. Moller, M.D., and Kurt Amplatz, M.D., 1975 Journal, vol. 125, No. 3.

Radiolgy, a monthly journal devoted to clinical radiology and allied sciences, vol. 131, Aprl.–Jun. 1979, The Radiological Society of North America.

*Primary Examiner*—William E. Kamm
*Attorney, Agent, or Firm*—Burns, Doane, Swecker & Mathis, LLP

[57] ABSTRACT

Disclosed is a method and apparatus to treat an aneurysm. The method involves the introduction of an embolic material into the aneurysm. The embolic material is adapted to permit tissue ingrowth within the region defined by the aneurysm, which results in treatment of the aneurysm. Preferred embolic materials are those having an open cell structure, such as polyvinyl alcohol foams. Also disclosed is a catheter which may be used to introduce an embolic material into an aneurysm.

17 Claims, 3 Drawing Sheets

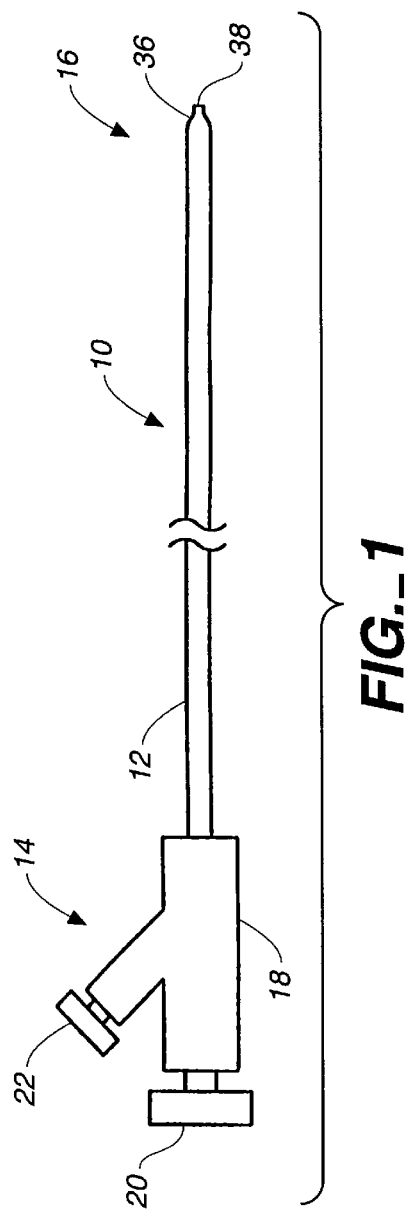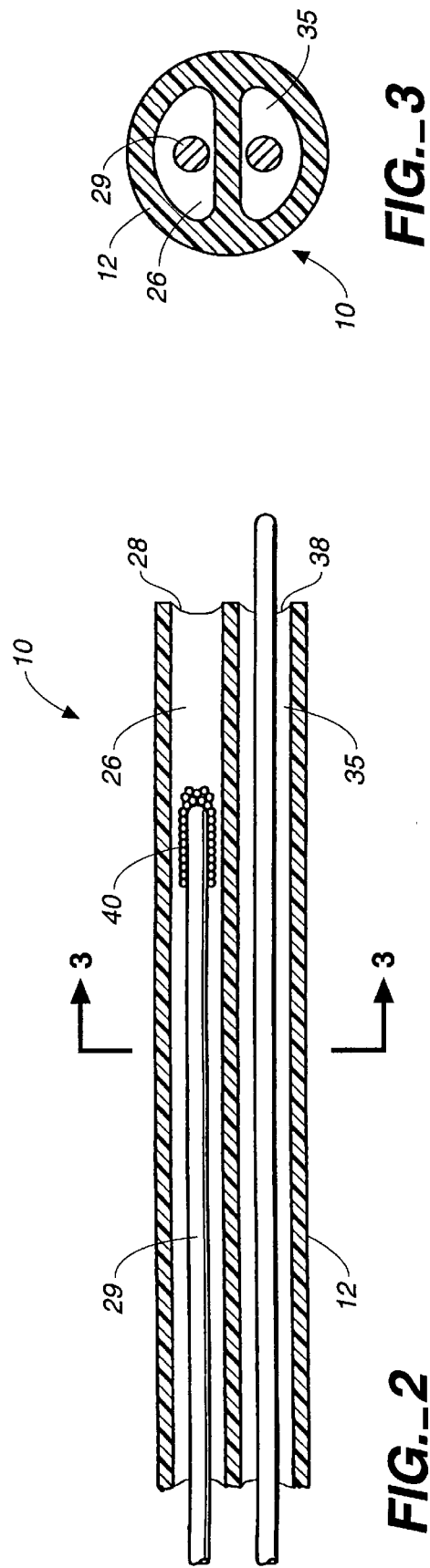

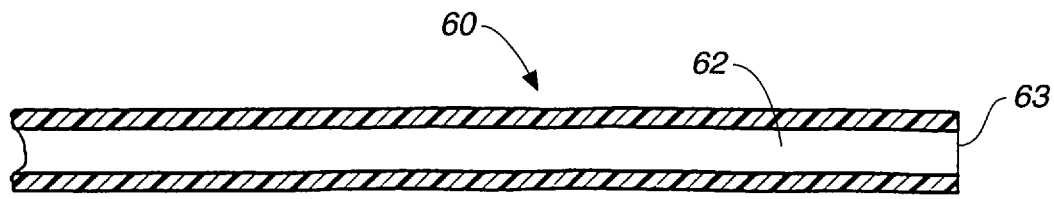
FIG._4
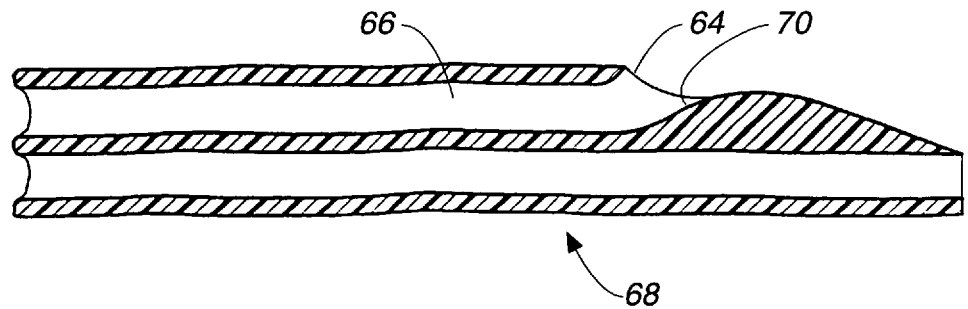
FIG._5
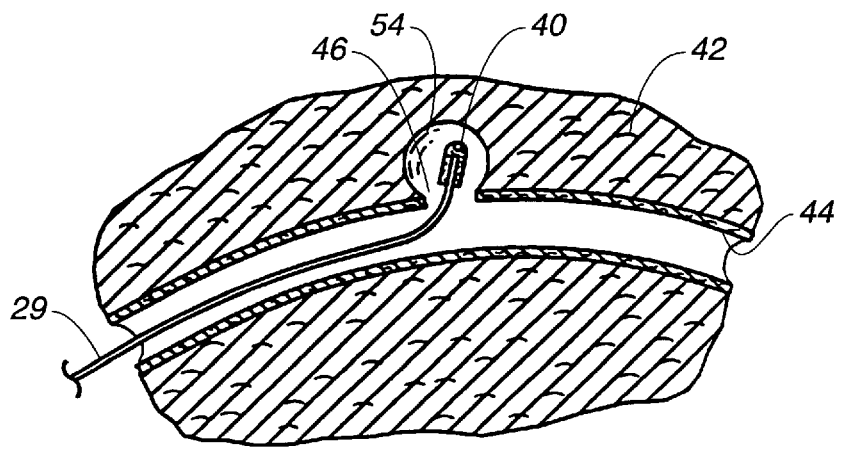
FIG._6A

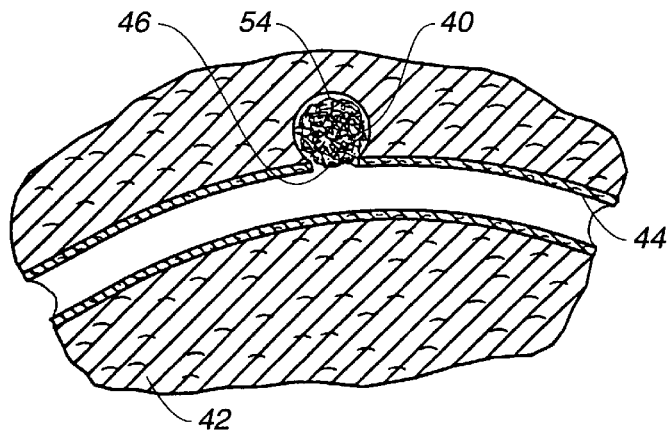
FIG._6B
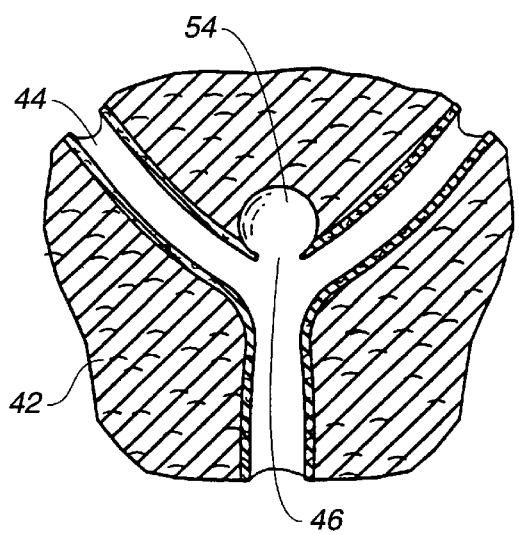
FIG._7
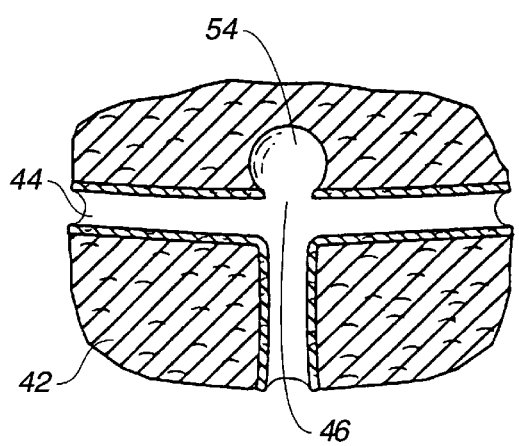
FIG._8

METHOD AND APPARATUS FOR INTRAVASCULER EMBOLIZATION

FIELD OF THE INVENTION

The present invention relates to intravascular embolization, and in one application, to a method and apparatus for inserting material into an aneurysmal sac to promote thrombus formation or other healing mechanisms within the sac, thereby treating the aneurysm.

BACKGROUND OF THE INVENTION

An aneurysm is a balloon-like swelling in the wall of a vessel. An aneurysm generally results in weakness of the vessel wall in which it occurs, which predisposes the region to a tear or rupture, with potentially catastrophic consequences for the patient. For example, if an aneurysm is present within an artery in the brain, and should burst under blood pressure, cranial hemorrhaging, and perhaps death, may occur.

Aneurysms may result from a variety of causes. For example, an aneurysm may result from trauma, from a degenerative disease which damages the muscular coat of a vessel, or it may be the result of a congenital deficiency in the muscular wall of the artery.

A variety of methods and apparatus have been used to provide an artificial structural support to the vessel region affected by the aneurysm, to minimize the effect of blood pressure and impact pressure within the aneurysmal sac, and thus prevent or minimize the chance of rupture. For example, U.S. Pat. No. 5,405,379 to Lane discloses a self-expanding cylindrical tube which is intended to span the aneurysm, resulting in isolation of the aneurysm from blood flow. One drawback with such devices, however, is that while they may reduce the risk that the aneurysm might rupture, they do not necessarily promote a healing response within the aneurysm. In addition, indwelling stents may increase the risk of thrombosis or embolism, and the wall thickness of the stent may undesirably reduce the fluid flow rate in the vessel. Indwelling stents or bypass structures are also generally straight along their length and cannot always be used to treat aneurysms at a bend in the artery or in tortuous vessels such as in the brain.

Another approach to the treatment of vascular aneurysms has been the use of vaso occlusion coils. In general, this technique involves the implantation of coiled fine metal wire into the aneurysm, to inhibit the flow of red blood cells. This can in turn promote thrombus formation. See, for example, U.S. Pat. No. 5,304,194 to Chee, et al.; U.S. Pat. No. 5,304,195 to Twyford, Jr., et al.; and U.S. Pat. No. 5,354,295 to Guglielmi, et al. However, this technique leaves a metal coil implanted within the patient which may compact, and migrate over time, and does not optimize the body's natural healing processes.

Thus, there exists a need for a method and apparatus for treating an aneurysm which takes advantage of the body's own healing responses to treat the aneurysm. Preferably, the treatment minimizes any interference with blood flow in the adjacent vessel, is useful in small diameter vessels, and can be used to treat aneurysms located on either straight or curved portions of the adjacent vessel.

SUMMARY OF THE INVENTION

The present invention provides a method and apparatus for treating aneurysms which advantageously utilizes the body's own thrombic responses to treat an aneurysm.

There is provided in accordance with one aspect of the present invention an expandable plug for treating a vascular aneurysm. The plug comprises a biocompatible material which is expandable from a first, constrained volume to a second, larger volume. Before placement at the treatment site, the expandable material is in the first, constrained volume and restrained therein by a blood-soluble restraining agent.

Preferably, the expandable material comprises an open-cell structure foam. In one embodiment the expandable material comprises crosslinked polyvinyl alcohol. The blood-soluble restraining agent comprises any of a variety of agents which are soluble in blood, such as polyvinyl alcohol, polyvinyl pyrrolidone, gelatin, or dextrose.

In accordance with another aspect of the present invention, there is provided a combination of a transluminal delivery wire and an expandable plug for treating a vascular site. The combination comprises an elongate flexible delivery wire having proximal and distal ends, and an expandable plug on the distal end of the delivery wire. The plug is expandable from a first, introduction volume to a second, expanded volume upon exposure to a body fluid. The expandable plug is initially releasably secured to the delivery wire in the first, introduction volume. The plug is released from the delivery wire and expands to the second, expanded volume upon exposure to a body fluid, and dissolution of the blood soluble restraining agent.

In one embodiment the expandable plug comprises a plurality of particles which are compressible from an expanded volume to a compressed volume. In another embodiment, the plug comprises a single particle of open cell foam material.

In accordance with a further aspect of the present invention, there is provided a method of making an expandable plug for delivery to a vascular aneurysm. The method comprises the steps of providing an elongate flexible delivery wire having proximal and distal ends, and providing an expandable plug material which is expandable from a first, compressed volume to a second, expanded volume. The material is exposed to a blood soluble restraining agent and compressed into the first, compressed volume and placed in contact with the distal end of the delivery wire. The restraining agent is permitted to restrain the material in the first, compressed volume and in contact with the delivery wire.

In accordance with a further aspect of the present invention, there is provided a method of delivering an expandable material to a treatment site within a vessel. The method comprises the steps of providing an elongate flexible delivery device having proximal and distal ends and an expandable material at the distal end. The distal end is transluminally advanced and positioned such that the material is at the treatment site. The material is exposed to a body fluid, causing blood to dissolve the restraining agent and the material to expand at the delivery site.

Further features and advantages of the present invention will become apparent to those of skill in the art in view of the disclosure which follows, when considered together with the attached drawings and claims.

BRIEF DESCRIPTION OF THE DRAWINGS

FIG. 1 is a side elevational view of a catheter adapted to introduce the aneurysm embolic material of the present invention.

FIG. 2 is a cross-sectional enlargement of the distal portion of a catheter of the present invention.

FIG. 3 is a cross-sectional view taken along the lines 3—3 of FIG. 2.

FIG. 4 is a cross-sectional enlargement of the distal portion of a single lumen embodiment of the catheter of the present invention.

FIG. 5 is a cross-sectional enlargement of the distal portion of a dual lumen catheter of the present invention, having a lateral exit port.

FIG. 6a is a schematic representation of a delivery wire having an embolic plug thereon positioned within a side wall aneurysm.

FIG. 6b is a schematic representation of the side wall aneurysm as in FIG. 6a, with the embolic plug in an expanded configuration.

FIG. 7 is a schematic representation showing the general orientation of a bifurcation aneurysm.

FIG. 8 is a schematic illustration showing the general orientation of a terminal aneurysm.

DETAILED DESCRIPTION OF PREFERRED EMBODIMENTS

Referring to FIG. 1, there is depicted catheter 10 for delivering the embolic plugs of the present invention. Although illustrated in a context of a simple catheter, having a single lumen (FIG. 4) or having a single guidewire lumen and a single delivery wire lumen (FIGS. 1–3 and 5), it is to be understood that the present method of treating aneurysms can readily be adapted to a wide variety of catheter structures, including those capable of performing additional functions not described herein. Similarly, although the present invention will be described primarily in the context of treating vascular aneurysms, the present inventors contemplate much broader potential applicability to any of a variety of conditions which would benefit from intravascular embolization as will be appreciated by those of skill in the art.

For example, the embolic delivery catheter may also be provided with an inflatable balloon and an inflation lumen, to permit vascular dilatation as is understood in the art. In addition to or instead of balloon dilatation capabilities, an inflatable balloon may be used to assist in holding the catheter in position while embolic plug is expressed into the aneurysm. A distal inflatable balloon may also be utilized to permit the catheter to float downstream directed by blood flow to position the catheter, as will be understood by those of skill in the art.

The catheter may also be provided with a delivery lumen with distal delivery openings through the wall of the catheter to enable the site specific introduction of medication, contrast media or other fluids. Catheters having any of a variety of functional capabilities can readily be adapted for use with the apparatus and method of the present invention, as will be apparent to those of skill in the art in view of the disclosure herein.

Catheter 10 generally comprises an elongate flexible tubular body 12 extending between a proximal control end 14 and a distal functional end 16. The length of the tubular body 12 depends upon the desired application. In general, tubular body 12 will have a generally circular cross-sectional configuration with an external diameter within the range of from about 0.026 inches to 0.065 inches for most cerebral vascular applications. Alternatively, a generally triangular cross-sectional configuration can also be used, depending upon the number of lumen in the catheter, with the maximum base to apex distance also generally within the range of from about 0.030 inches to about 0.065 inches. Other noncircular catheter configurations, such as rectangular or oval, may also be used to introduce the embolic plugs of the present invention. In peripheral vascular applications, tubular body 12 will typically have an outside diameter within the range of from about 0.026 inches to about 0.091 inches.

The present invention is particularly suited for treating intracranial vascular aneurysms. For intracranial applications, the percutaneous access site is generally the femoral artery. Catheters having an axial length within the range of from about 150 cm to about 175 cm are generally preferred for this application. The maximum outside diameter of at least the distal segment of the catheter is limited by the inside diameter of the target vessel. In general, catheters having a diameter of no more than about 0.052 inches, and preferably no more than about 0.038 inches are preferred for most intracranial applications of the present invention.

Catheters having diameters outside the ranges recited above may also be used with the embolic plugs of the present invention, provided that the functional consequences of the diameter are acceptable for the specific intended use of the catheter. For example, the lower limit of the diameter for tubular body 12 in a given application will be a function of, among other things, the number of desired functional lumen contained in the catheter.

In addition, tubular body 12 must have sufficient structural integrity (i.e., "pushability") to permit the catheter to be advanced to distal arterial locations without buckling or undesirable bending of tubular body 12. The ability of tubular body 12 to transmit torque may also be desirable, such as in those embodiments where it may be desirable to rotate the tubular body 12 after insertion, as for example, to facilitate advancing a plug introduction wire laterally into an aneurysmal sac, as discussed below.

Catheters having larger tubular body diameters may be provided with larger internal lumen, thereby facilitating movement of wires or fluids therein, but such larger diameters will tend to reduce perfusion in the artery in which the catheter is placed, and for certain applications, will be too large to be used in small diameter vessels. Increased diameter catheter bodies also tend to exhibit reduced flexibility, which can be disadvantageous for treatment of aneurysms in a remote or tortuous vascular location.

The proximal end 14 of catheter 10 may be provided with a manifold 18 having one or a plurality of access ports, as is known in the art. As depicted in FIG. 1, manifold 18 is provided with a guidewire port 20 in an "over-the-wire" guidewire embodiment. Manifold 18 also features a side port 22 for introduction of a plug delivery wire 29 in a dual lumen embodiment.

The distal end 16 of the catheter 10 is preferably provided with an atraumatic distal tip 36, as is known in the art. One or more radiopaque markers may also be provided to facilitate positioning of the catheter. Radiopaque markers may be provided proximally and distally of exit port 64, (in a laterally opening embodiment) so that exit port 64 may be readily positioned adjacent an aneurysmal sac. Suitable marker bands can be produced from any of a variety of materials, including platinum, gold, and tungsten\rhenium alloy, and alloys thereof.

Referring to FIGS. 1 and 2, guidewire port 20 is in communication with a guidewire lumen 35, which extends axially along the length of catheter 10. An opening 38 is provided at or near the distal end of the catheter for providing exterior access to the guidewire lumen 35. The proximal guidewire port 20 may be eliminated from manifold 18 in a rapid-exchange or "monorail" embodiment, in which embodiment the proximal opening of the guidewire lumen 35 is positioned along the side of tubular body 12. The proximal guidewire access port in a rapid exchange embodiment for coronary vascular applications is typically within about 20 cm from the distal end of the catheter.

Plug wire port 22 is in communication with lumen 26, which extends axially along the length of catheter 10 in a dual lumen embodiment. An exit port 28 is provided at or near the distal end 16 of catheter 10 to permit the distal end of plug wire 29 to exit the tubular body and enter the aneurysm.

As illustrated in FIG. 2, plug wire 29 is slidably receivable within lumen 26. An embolic plug 40 is attached to the distal tip of plug wire 29 in a manner which permits release of embolic plug 40 from wire 29 when wire 29 is exposed to body fluids, such as blood or plasma.

The embodiment illustrated in FIGS. 2 and 3 is a side by side dual lumen catheter. This catheter may be desirable in applications where a guidewire is utilized to assist in advancing the catheter to the treatment site, and in which the clinician desires that the guidewire be left in place throughout the procedure. A separate lumen is therefore desirable to permit distal advance of the plug introduction wire 29.

Alternatively, the plug introduction wire is introduced through the same lumen as the guidewire. Referring to FIG. 4, there is disclosed a distal section of a single lumen catheter 60 useful for this purpose. This catheter design may be desirable in applications where a guidewire is not necessary to advance the distal tip of the catheter to the treatment site. Alternatively, the embodiment of FIG. 4 may be utilized where the catheter is advanced over a guidewire to the treatment site, but the guidewire may be removed following proper placement of the catheter. Central lumen 62 is then available to receive the plug introduction wire axially therethrough. The introduction wire is then advanced distally through the lumen, and the distal plug is positioned in the aneurysm. Upon exposure to blood, the plug expands in the aneurysm and is released from the wire.

One advantage of catheters built in accordance with the design of FIG. 4 is that the outside diameter of the catheter may be minimized due to the single lumen construction. Single lumen construction may be utilized in catheters either designed for sequential guidewire and plug introduction wire use, as described above, or also for simultaneous guidewire and plug introduction wire use. Thus, the inside diameter of lumen 62 may be sufficiently large to accept both a placement guidewire and a plug introduction wire in a slidable side by side relationship within lumen 62.

Preferably, the single lumen embodiment of FIG. 4 has an internal diameter which is no larger than necessary to slidably receive the plug wire having a plug in the reduced, introduction diameter thereon. Particularly for cranial vascular applications, the outside diameter of the introduction catheter is preferably minimized. In a single lumen catheter of the type illustrated in FIG. 4, the proximal manifold may be simplified by eliminating the side port 22. Alternatively, a side port may be provided, if desired, to permit introduction of a contrast media through the central lumen 62 such as to permit fluoroscopic evaluation of the size of the aneurysm.

Referring to FIG. 5, there is disclosed an alternate dual lumen embodiment of the introduction catheter of the present invention. This embodiment is similar to that illustrated in FIG. 2, except that the distal opening 64 of plug introduction wire lumen 66 opens laterally from the side of the catheter 68. A gentle lateral ramp 70 may also be provided to assist in launching the plug introduction wire in a lateral direction relative to the catheter.

The catheters illustrated in FIG. 2 through 5 can be constructed in any of a variety of manners well known in the catheter construction art. For example, the catheter of the present invention may be produced by extrusion techniques using high or medium density polyethylene or any of a variety of other catheter body materials well known in the art. Alternatively, the catheter body may be fabricated such as through the use of wire wound or polymeric ribbon wound coil structures. The selection of any particular catheter body construction technique will be governed by the intended use of the catheter, and the resulting dimensional and physical property requirements imposed by that use as has been discussed.

Aneurysms may form at any of a variety of locations within the vascular system. For example, an aneurysm may form on the side wall of a relatively straight arterial flow path. See, for example, FIG. 6*a*. This type of aneurysm can be accessed either by a catheter or introduction wire which can advance in a lateral direction relative to the longitudinal axis of the vessel or by a very flexible distal tip catheter.

Lateral launching of the embolic plug can be accomplished through the use of a catheter having a lateral opening therein, and/or by the use of a thrombic plug wire having a laterally bent distal tip. Similarly to the memory contained in most guidewires, a prebent distal tip on the delivery wire of the present invention will tend to exert a lateral biasing force against the wall of the delivery lumen. Once the wire is advanced distally out of the catheter, the prebent tip will tend to return to its prebent configuration, thereby exerting a lateral bias against the wall of the vessel. In this manner, and by torquing the wire to assume the proper rotational orientation, the plug can be steered into an aneurysm. The use and functionality of prebent distal tips on guidewires will be well understood to those of ordinary skill in the art in view of conventional percutaneous transluminal coronary angioplasty guidewire placement techniques.

Aneurysms occasionally form at a branch point where a single artery divides into two or more branches. See, for example, FIGS. 7 (bifurcation aneurysm) and 8 (terminal aneurysm). Due to the pressure exerted by blood flow, such aneurysms often form directly in the line of flow of blood from the primary artery, in between the two branches. This type of aneurysm can be readily accessed by a distally opening catheter such as that illustrated in FIG. 2 or FIG. 4.

As will be discussed below, the preferred plug material is a compressed crosslinked PVA foam material which will expand and become disassociated from the introduction wire upon contact with blood or other bodily fluid and dissolution of restraining agent. Thus, the compressed PVA foam or other particles should not have a sufficient exposure to blood prior to placement within the aneurysm or the plug may prematurely expand. A variety of features of the catheters, plug coating and or methods of the present invention can be utilized to minimize the risk of premature expansion or disassociation of the embolic material.

In one embodiment, a liquid-tight pierceable membrane (not illustrated) is placed over exit port 28 or 64, such that the plug introduction lumen is not exposed to internal body fluids until delivery wire 29 is forced distally through the membrane. In this embodiment, the membrane may function to protect certain types of embolic materials useful for practicing the present invention from expanding prematurely, as will be discussed below. The membrane may be fashioned out of any of a variety of pierceable biocompatible materials known to those of skill in the art, such as polyethylene or polypropylene, and be attached by bonding or fusion, or be integrally formed with the catheter tubular body. The membrane is preferably fluid tight, and also pierceable by wire 29 without displacing any embolic material attached to wire 29.

Alternatively, a biodegradable or soluble membrane or plug may be positioned in the distal end of the delivery lumen. By gradually dissolving upon contact with blood, the plug would provide a sufficient barrier between the embolic inside the catheter and the blood stream to permit placement of the catheter. The thickness and composition of the membrane or plug can be selected to provide a predetermined dissolution time to permit catheter placement before the embolic material becomes exposed to blood.

By sealing the proximal opening of the delivery lumen around the delivery wire, a hydrostatic lock of a small volume of a biologically compatible fluid which will not readily dissolve the restraining agent such as saline/glycerine can be maintained in the catheter at least between the distal end of the delivery wire and the distal opening of the delivery wire lumen. A slight positive pressure on such a protective fluid can also be maintained. Following placement of the catheter, the delivery wire can be advanced distally out of the distal end of the catheter and into the aneurysm.

As a further alternative, the delivery wire having embolic material secured thereto can simply be maintained apart from the catheter, and only inserted into the catheter and advanced transluminally to the aneurysm after the catheter has been appropriately positioned within the vessel.

The embolic materials useful for practicing the present invention are preferably biocompatible materials having an open cell structure to which cells may bind to stimulate embolization and thrombosis. Although a wide variety of materials may be used, certain properties appear desirable. For example, low compression set materials are preferred. Molecular weights typically will fall within the range of from about 50,000 to 500,000 and preferably from about 100,000 to about 200,000. A modulus within the range of from about 10,000 to about 100,000 psi and preferably no more than about 50,000 psi. Substantially open cell foam structure is preferred, and as high as 90% open cell or even higher is preferable.

Presently preferred materials include crosslinked polyvinyl alcohol (PVA) foam, also known as Ivalon, polyurethane foam, polyethylene foam, silicone foams or fluorinated polyolefin foams. A variety of other biodegradable materials may also be used. Biodegradable for the present purpose generally means degraded/eroded in the body over a period of a few days to several months. These materials are selected with the expectation that they will be non-permanent in specific clinical situations. Suitable biodegradable materials for this purpose include gelatin—(Gelfoam); collagen—(Avitene); oxidized, modified cellulose—(Oxycel); poly lactic acid, glycolic acid and copolymers; polycaprolactone and copolymers; poly ethylene glycol, propylene glycol and copolymers; polyvinylpyrrolidone and copolymers; poly (vinyl alcohol) and copolymers; and modified starches. Autologous tissue (clot, fat, etc.) may not be appropriate in a foam structure, but may be compressible and useful in some applications. As will be appreciated by one of skill in the art in view of the present disclosure, any of a variety of materials which permit or facilitate embolization may be used in place of PVA foam.

When PVA foam is used to make embolic plug 40, it is preferably formed into roughly spherical pellets having uncompressed diameters which range from about 1 mm to about 10 mm, more preferably from about 3 mm to about 6 mm, and most preferably from 3–4 mm in diameter. A sufficient number of pellets to produce the desired total expanded volume is then secured to the delivery wire as discussed below. Other pellet sizes may be appropriate for other embolic plug materials depending upon compressibility and expansion characteristics, as can be readily determined by one of skill in the art for a given application. It should be appreciated, that the particles used to form embolic plug 40 may be formed in any of a variety of shapes, such as cubes, cylinders, or nonregular shapes, and may still be used to practice the present invention.

As will be appreciated by those of skill in the art, the number of particles utilized to construct a plug 40 may be varied considerably, depending on a variety of considerations such as the size of the aneurysm to be treated, the composition of the particles, the desired time release characteristics of the plug or others that will be understood by those of skill in the art. A single particle of material sized to treat the aneurysm may desirably minimize the risk of post-installation migration.

For certain applications, it may be desirable to use particles of larger sizes than those described, such as when treating giant aneurysms. The optimal size of the particle or particles for a desired plug will depend in part upon the relative compressibility of the material selected and the size of the intended aneurysm to be treated. For example, a single foam particle having an expanded cross section on the order of no more than about 12 mm may be useful to treat small aneurysms. Large aneurysms may use a particle having a cross section within the range of from about 12 mm to about 24 mm and particles greater than about 25 mm may be used to treat giant aneurysms. Optimization of particle and plug size in view of a particular compressible material and particular aneurysm can be readily accomplished by one of skill in the art in view of the disclosure herein.

Embolic plug 40 may be attached to wire 29 by any of a variety of ways which permit the clinician to release the plug 40 at the desired location. In one method of attachment, one or more roughly spherical embolic particles are formed from crosslinked PVA foam, and are wetted with a blood soluble restraining agent, such as a 10–20 weight % concentration aqueous solution of polyvinyl alcohol or polyvinyl pyrrolidone. The desired volume of one or more moistened particles are then placed adjacent to plug wire 29 and the assembly is inserted into a press. The particles are compressed onto the surface of the wire, reducing their size by a factor of at least about 5 and preferably from about 10 to 15, and are then allowed to dry. Once dry, the restraining agent functions to retain the particles in the compressed state and in attachment to wire 29 in the form of an expandable plug. However, because the restraining agent is blood soluble, once wire 29 bearing plug 40 is exposed to blood within the body, plug 40 will reconstitute to the uncompressed state. Moreover, the restraining agent bond between plug 40 and wire 29 will be broken, releasing plug 40 within the aneurysm.

In one embodiment, the compressed embolic material is provided with a time release coating which may be the same as or in addition to the restraining agent. The time release coating may be applied such as by dipping or spraying processes as can be readily devised by those of skill in the art. The coating composition and thickness is selected to permit a predetermined exposure time to blood before it is dissolved sufficiently to permit expansion of the embolic plug. In this manner, the invention can be readily practiced without the need for specially designed introduction catheters.

In an alternate mode of the invention, the embolic plug is expandable from the first, reduced volume to the second, implanted volume without the need for a chemical restraining agent. In this embodiment of the invention, the embolic plug material is compressed and loaded into a delivery catheter such as central lumen 62 of catheter 60 (FIG. 4). The catheter 60 functions as a restraining sleeve, to restrain the embolic material in its compressed form. Following placement of the distal end of the catheter at or about the opening to the aneurysm, a pushwire is advanced distally through the central lumen 62 to push the compressed embolic material out the distal end of the catheter. Other restraining sleeve variations for restraining the compressed embolic material in its compressed configuration will be readily apparent to those of skill in the art in view of the disclosure herein.

One advantage of the expandable foam embolic material of the present invention over prior art expandable indwelling materials is the relatively low radially outwardly directed biasing force exerted by the reconstituted foam. One disadvantage of memory metal coils and other self expanding gels is the possibility of exerting an excessive radially outwardly directed force upon expansion. Excessive forces can increase the risk of rupture, particularly if the expanded volume of the material is to large for a particular aneurysm. The relatively low force exerted by the expanding foam of the present invention minimizes the risk of rupture or dissection of the artery as a result of the expansion.

Due to the variation in size and configuration of aneurysms from patient to patient and from aneurysm to aneurysm, delivery wires having an expandable material thereon are preferably provided in an array of different implantation and expanded sizes for selection by the clinician. For example, wires having an expanded volume foam as low as about 0.015 cc, and as high as about 8 cc in an unconstrained expansion may be provided. Intermediate volumes may also be provided, so that the clinician has a series of graduated plug wires to choose from.

In general, the clinician will select a plug which has an expanded volume in the unconstrained state of greater than the anticipated volume of the aneurysm to reduce the risk of migration out of the aneurysm. For example, the unconstrained expanded plug volume may exceed the aneurysm volume by as much as about 25% or greater. The size of the aneurysm can be approximated fluoroscopically with injection of contrast media into the aneurysm, as will be understood by those of skill in the art. The relatively low expansive force of the preferred expanded foam enables the use of larger volume foams which, when constrained by the aneurysm, stop expanding and conform to the interior thereof.

The use of the embolic plug wire 29 and plug 40 of the present invention in the context of treating a vascular aneurysm can be readily understood by reference to FIGS. 6a and 6b. Referring to FIG. 6a, there is illustrated a section of tissue 42 having a vessel such as an artery 44 extending therethrough. A portion of the wall of the vessel 44 has formed an opening 46 into an aneurysm 54. In this illustration, a prebent plug wire 29 has been navigated through the opening 46 and into the aneurysm 54. The plug wire 49 is provided with an expandable plug 40, illustrated in its reduced, introduction volume. The particular introduction catheter utilized to facilitate placement of the plug 40 within the aneurysm 54 is relatively unimportant, and was therefore not illustrated in FIG. 6a.

In practice, the clinician inserts an introduction catheter using standard medical procedures known to those of skill in the art, and positions the catheter such that a distal opening on a delivery lumen is adjacent the aneurysm 54. If necessary, plug wire 29 may be prebent and rotated (torqued) so that the distal tip of plug wire 29 faces the aneurysmal opening. Plug wire 29 is then advanced so that the distal tip of plug wire 29 enters the aneurysmal sac 54. See FIG. 6a.

The embolic plug 40 will begin to expand when exposed to the bodily fluids contained in the aneurysmal sac 54. Expansion can commence almost immediately or after a time delay depending upon the restraining agent and degree of compression. As plug 40 expands, it will detach from wire 29 and continue to expand until it reaches its native size and configuration, or its expanded configuration as constrained by the surrounding anatomy. See FIG. 6b.

Wire 29 is withdrawn back through opening 46, leaving the embolic plug 40 in place within the aneurysmal sac 54, and the catheter and wire assembly 29 is removed. Because of the open cell structure of the embolic plug, it is readily invaded by fibrous tissues, and will promote embolization within the aneurysmal sac. Clot promoting agents such as fibrin, fibrinogen or thrombin can be impregnated into the foam structure to enhance embolization as will be appreciated by those of skill in the art.

Compressed crosslinked/polyethylene, PVA, or other expandable foam plugs can be delivered using vehicles other than attachment to a delivery wire. For example, a compressed foam plug can be inserted into the proximal end of a delivery lumen and advanced transluminally in a distal direction to the treatment site using a pusher wire. Alternatively, the compressed foam plug can be prepositioned within the delivery lumen such as at the point of manufacture, and pushed from the distal opening of the lumen and into the aneurysm using a pushwire, or by the introduction of pressurized fluids such as saline behind the plug to advance the plug distally from the catheter into the aneurysm.

A variety of alternative materials can be utilized for making an aneurysm-treating plug, as long as the material can be provided in a manner that is introducible in a first, reduced volume and capable of growing to a second, larger volume within the aneurysm. In addition, the particle or particles which are compressed to form a plug can be impregnated with a drug for localized drug delivery at the treatment site. Open-cell foam structures can be immersed in an aqueous solution of the drug prior to compression into an aneurysm-treating plug. Alternatively, any of a variety of known binding techniques for releasably binding a drug to a carrier can be utilized, as will be apparent to those of skill in the art.

In addition, any of a variety of restraining agents or cements can be utilized, depending upon the underlying particle composition and structure. Selecting an appropriate plug material and restraining agent pair can be readily accomplished through routine experimentation by those of skill in the art. Suitable restraining agents for use with PVA plugs, for example, include gelatin, natural gums, dextrose, sugar, polysaccharides (HEstarch), water soluble polymers and others which can be identified through routine experimentation.

Plug material, structure and compression can affect the length of time between the first exposure to blood and the time that the plug is fully expanded within the aneurysm. For example, tailoring the compression ratio, such as by compressing the material to a greater density, can prolong the length of time required to fully release once exposed to an aqueous media. As an alternative, or in addition to increased compression, additional layers of the restraining agent can be applied over the compressed plug to slow the release time for the plug. The concentration of the restraining agent can also be increased to delay the onset of or slow plug expansion, and the chemical composition of the restraining agent can be modified to reduce its rate of solubility in blood.

Depending upon the particular combination of restraining agent, compression, and concentration or loading of the restraining agent, any of a variety of desired release times can be obtained. In general, it is presently preferred that the expansion time for the plug fall within the range of from about 30 seconds to as much as 15 minutes, depending upon the mode of delivery of the plug and how long it will likely be exposed to blood before the clinician will have ample time to properly position the plug within the target aneurysm.

It will be appreciated that certain variations of the present invention may suggest themselves to one of ordinary skill in the art. The foregoing detailed description is to be clearly understood as given by way of illustration, the spirit and scope of this invention being limited solely by the appended claims.

What is claimed is:

1. An expandable plug for treating a vascular aneurysm, comprising:
    a biocompatible material, expandable from a first constrained volume to a second, larger volume; and
    a blood soluble restraining agent in contact with the expandable material; wherein the expandable material is in the first, constrained volume and restrained therein by the blood soluble agent.

2. An expandable plug as in claim 1, wherein the expandable material comprises an open cell structure foam.

3. An expandable plug as in claim 1, wherein the expandable material comprises polyvinyl alcohol.

4. An expandable plug as in claim 1, wherein the expandable material is selected from the group consisting of polyurethane foam and polyethylene foam.

5. An expandable plug as in claim 1, wherein the agent is selected from the group consisting of polyvinyl alcohol, polyvinyl pyrrolidone, gelatin, natural gums, dextrose, sugar, and polysaccharides.

6. An expandable plug as in claim 1, wherein the second, larger volume is larger than the first constrained volume by a factor of at least about 5.

7. An expandable plug as in claim 6, wherein the second, larger volume is larger than the first constrained volume by a factor of at least about 10.

8. An expandable plug as in claim 1, wherein the expandable material comprises a plurality of particles of material secured together by the agent.

9. An expandable plug as in claim 8, wherein at least some of the particles have an expanded cross-sectional dimension within the range of from about 1 mm to about 10 mm.

10. The combination of a transluminal delivery wire and expandable plug for treating a vascular site, comprising:
    an elongate flexible delivery wire having proximal and distal ends; and
    an expandable plug on the distal end of the delivery wire;
    wherein the expandable plug is expandable from a first introduction volume to a second expanded volume upon exposure to a body fluid; and
    the expandable plug is releasably secured to the delivery wire such that the plug is released from the delivery wire upon exposure to a body fluid.

11. The combination of a transluminal delivery wire and expandable plug as in claim 10, wherein said plug comprises a plurality of particles which are compressible from an expanded volume to a compressed volume.

12. The combination of a transluminal delivery wire and expandable plug as in claim 11, wherein said particles have cross-sectional dimensions within the range of from about 3 mm to about 6 mm.

13. The combination of a transluminal delivery wire and expandable plug as in claim 10, wherein said plug comprises a biocompatible material having an open cell structure.

14. The combination of a transluminal delivery wire and expandable plug as in claim 10, wherein the expandable plug is selected from the group consisting of polyvinyl alcohol foam, polyurethane foam, and polyethylene foam.

15. An expandable plug delivery system comprising:
    a biocompatible material plug expandable from a first constrained volume to a second, larger volume;
    a blood soluble restraining agent in contact with the expandable material plug;
    wherein the expandable material plug is in the first, constrained volume and restrained therein by the blood soluble agent; and
    wherein the biocompatible material plug is releasably secured to a distal end of an elongate flexible delivery wire.

16. The expandable plug delivery system as in claim 15, wherein the expandable plug is secured to the flexible delivery wire by the blood soluble agent.

17. The expandable plug delivery system as in claim 16, wherein the expandable plug is releasable from the delivery wire upon exposure to a body fluid.

* * * * *